(12) United States Patent
Mussler et al.

(10) Patent No.: US 10,905,733 B2
(45) Date of Patent: Feb. 2, 2021

(54) WATER SOLUBLE TOMATO EXTRACT PROTECTS AGAINST ADVERSE EFFECTS OF AIR POLLUTION

(71) Applicant: Provexis Natural Products Limited, Reading (GB)

(72) Inventors: Bernd Mussler, Kaiseraugst (CH); Daniel Raederstorff, Kaiseraugst (CH); Nathalie Richard, Kaiseraugst (CH)

(73) Assignee: Provexis Natural Products Limited, Reading (GB)

( * ) Notice: Subject to any disclaimer, the term of this patent is extended or adjusted under 35 U.S.C. 154(b) by 86 days.

(21) Appl. No.: 16/346,013

(22) PCT Filed: Nov. 2, 2017

(86) PCT No.: PCT/EP2017/077993
§ 371 (c)(1),
(2) Date: Apr. 29, 2019

(87) PCT Pub. No.: WO2018/083137
PCT Pub. Date: May 11, 2018

(65) Prior Publication Data
US 2020/0054706 A1    Feb. 20, 2020

(30) Foreign Application Priority Data
Nov. 2, 2016    (EP) .................................... 16196794

(51) Int. Cl.
*A61K 36/00* (2006.01)
*A61K 36/81* (2006.01)
*A23L 33/105* (2016.01)

(52) U.S. Cl.
CPC ............ *A61K 36/81* (2013.01); *A23L 33/105* (2016.08)

(58) Field of Classification Search
CPC ....................................................... A61K 36/00
See application file for complete search history.

(56) References Cited

U.S. PATENT DOCUMENTS

| | | | |
|---|---|---|---|
| 4,925,690 | A | 5/1990 | Odake |
| 5,502,038 | A | 3/1996 | Malinow |
| 6,436,452 | B1 | 8/2002 | Duetz et al. |
| 6,780,444 | B1 | 8/2004 | Reza |
| 6,958,164 | B2 | 10/2005 | Dutta-Roy |
| 2003/0206983 | A1 | 11/2003 | Dutta-Roy |
| 2004/0191790 | A1 | 9/2004 | Tomassen et al. |
| 2004/0223962 | A1 | 11/2004 | Riordan |
| 2005/0153038 | A1 | 6/2005 | Giori |
| 2006/0035971 | A1 | 2/2006 | Youichi et al. |
| 2006/0078632 | A1 | 4/2006 | Woo et al. |
| 2006/0084614 | A1 | 4/2006 | Eckl et al. |
| 2006/0154877 | A1 | 7/2006 | Liu et al. |
| 2007/0082071 | A1 | 4/2007 | Willimann |
| 2007/0259059 | A1 | 11/2007 | Eidenberger |
| 2008/0009449 | A1 | 1/2008 | Prasad |
| 2009/0053340 | A1 | 2/2009 | Crosbie |
| 2009/0123584 | A1 | 5/2009 | O'Kennedy |
| 2011/0206794 | A1 | 8/2011 | O'Kennedy |
| 2011/0212913 | A1 | 9/2011 | O'Kennedy |
| 2012/0321732 | A1 | 12/2012 | O'Kennedy |
| 2013/0023489 | A1 | 1/2013 | Kubow et al. |
| 2014/0147537 | A1 | 5/2014 | O'Kennedy |
| 2015/0105338 | A1 | 4/2015 | O'Kennedy |
| 2015/0132371 | A1 | 5/2015 | Duttaroy |
| 2016/0375080 | A1 | 12/2016 | O'Kennedy |
| 2018/0256666 | A1 | 9/2018 | O'Kennedy |
| 2018/0271926 | A1 | 9/2018 | Duttaroy |

FOREIGN PATENT DOCUMENTS

| | | |
|---|---|---|
| CN | 1352941 | 6/2002 |
| CN | 1650951 | 8/2005 |
| DE | 19720767 A1 | 11/1998 |
| EP | 1334728 A2 | 8/2003 |
| EP | 1481669 A1 | 12/2004 |
| EP | 1508325 A1 | 2/2005 |
| EP | 1559421 A1 | 8/2005 |
| EP | 1640001 A1 | 3/2006 |
| EP | 2036568 A1 | 3/2009 |
| FR | 2871378 A1 | 12/2005 |
| JP | 05-201846 A | 8/1993 |
| JP | H09-009892 A | 1/1997 |
| JP | 03-004769 | 1/1999 |
| JP | 2004-137287 | 5/2004 |
| JP | 2004-315386 A | 11/2004 |
| JP | 2006-193435 A | 7/2006 |
| JP | 2007-037530 A | 2/2007 |
| JP | 2009-240191 A | 10/2009 |
| JP | 2009-538895 A | 11/2009 |
| JP | 2012-36195 A | 2/2012 |
| JP | 2012-506901 A | 3/2012 |
| WO | WO 94/03421 A2 | 2/1994 |
| WO | WO 99/55350 A1 | 11/1999 |
| WO | WO 00/21507 A2 | 4/2000 |
| WO | WO 2006/085115 A2 | 8/2006 |
| WO | WO 2006/094120 A2 | 9/2006 |
| WO | WO 2007/141495 A1 | 12/2007 |
| WO | WO 2008/080162 A2 | 7/2008 |
| WO | WO 2008/131047 A2 | 10/2008 |

(Continued)

OTHER PUBLICATIONS

PCT/GB2006/000521 International Search Report and Written Opinion dated Aug. 10, 2006; 9 pages.

(Continued)

*Primary Examiner* — Michael V Meller
(74) *Attorney, Agent, or Firm* — Linda B. Huber; Nixon Peabody LLP

(57) ABSTRACT

The present invention relates to compositions comprising a water soluble tomato extract (WSTE) which may be used in maintaining cardiovascular health, lessening the risk of developing cardiovascular health problems, or reducing the likelihood of worsening an existing cardiovascular health problem in a subject exposed, or is at risk of exposure, to particulate air pollution.

6 Claims, 1 Drawing Sheet

(56) References Cited

FOREIGN PATENT DOCUMENTS

| WO | WO 2010/049707 A2 | 5/2010 |
|---|---|---|
| WO | WO 2010/049709 A2 | 5/2010 |
| WO | WO 2013/163057 A1 | 10/2013 |
| WO | WO 2014/102546 A1 | 7/2014 |
| WO | WO 2018/083137 A1 | 5/2018 |

OTHER PUBLICATIONS

PCT/GB2006/000521 International Preliminary Report on Patentability dated Aug. 14, 2007; 7 pages.
PCT/GB2007/002034 International Search Report and Written Opinion dated Oct. 29, 2007; 10 pages.
PCT/GB2007/002034 International Preliminary Report on Patentability dated Dec. 3, 2008; 8 pages.
PCT/GB2009/002593 International Search Report and Written Opinion Aug. 10, 2011; 17 pages.
PCT/GB2009/002593 International Preliminary Report on Patentability dated Oct. 11, 2011; 10 pages.
PCT/GB2009/002595 International Search Report and Written Opinion dated Apr. 26, 2010; 25 pages.
PCT/GB2009/002595 International Preliminary Report on Patentability dated May 3, 2011; 18 pages.
PCT/GB2013/053431 International Search Report and Written Opinion dated Feb. 7, 2014; 11 pages.
PCT/GB2013/053431 International Preliminary Report on Patentability dated Jun. 30, 2015; 8 pages.
PCT/US2013/037524 International Search Report and Written Opinion dated Jul. 8, 2013; 11 pages.
PCT/US2013/037524 International Preliminary Report on Patentability dated Oct. 28, 2014; 8 pages.
PCT/EP2017/077993 International Search Report and Written Opinion, dated Jan. 23, 2018, 10 Pages.
Chinese Patent Application No. 2007800204350 Examination Report; 12 pages.
GB Application No. 1223365.6 UKIPO Search Report. dated Jun. 12, 2013; 2 pages.
EP Application No. 07733050.4, Exam Report, dated Jan. 13, 2012, 7 pages.
Abbey et al. Effect of Quercetin Supplementation on Repeated-Sprint Performance, Xanthine Oxidase Activity, and Inflammation. International Journal of Sport Nutrition and Exercise Metabolism (2011). 91-96.
Abushita et al., Determination of Antioxidant Vitamins in Tomatoes. Food Chemistry (1997), 60(2):207-212.
Amagase et al. Lycium barbarum Attenuates Increased Plasma Stress Hormone Levels Induced by a Short and Intense Exercise Challenge. A Randomized, Double-blind, Placebo-controlled Human Clinical Study. FASEB Journal (2009). 23: 2 pages. Abstract Only.
Anthon et al., Thermal inactivation of pectin methylesterase, polygalacturonase, and peroxidase in tomato juice. Journal of Agriculture and Food Chemistry (2002), 50:6153-6159.
Bohm et al., Intestinal absorption of lycopene from different matrices and interactions to other carotenoids, the lipid status, and the antioxidant capacity of human plasma. European Journal of Nutrition (1999), 38(2):1436-6207. Abstract Only.
Burton-Freeman et al. Protective activity of processed tomato products on postprandial oxidation and inflammation: A clinical trial in healthy weight men and women. Mol. Nutr. Food Res. (2012). 56:622-631.
Castell et al. Granule Localization of Glutaminase in Human Neutrophils and the Consequence of Glutamine Utilization for Neutrophil Activity. The Journal of Biological Chemistry (2004). 279(14):13305-13310.
Cermak et al. Nitrate Supplemantation's Improvement of 10-km-Time-Trial Performance in Trained Cyclists. International Journal of Sport Nutrition and Exercise Metabolism (2012). 22:84-91.

Chaouat et al., The Role of Thrombosis in Severe Pulmonary Hypertension, European Respiratory Journal, 1996, vol. 9, pp. 356-363.
De Leeuw et al. Tomato Extract for Hypertension? Cardiovasc Drugs Ther (2009). 23:107-108.
dietandfitnesstoday.com Tomatoes Folic Acid Content, downloaded from the internet on Oct. 30, 2017, 14 pages.
Dutta-Roy et al. Effects of tomato extract on human platelet aggregation in vitro. Platelets (2001), 12(4):218-227.
Franklin, S.J., GRAS Exemption Claim: Claim of Exemption from the Requirement for Premarket Approval Pursuant to Proposed 21 CFR Section 170.36 (c)(1) [62 FR 18938 (Apr. 17, 1997) for Water-Soluable Tomato Concentrate (WSTC), Prepared by Provexis, 2006, 74 pages.
Friedman et al., Feeding tomatoes to hamsters reduces their plasma low-density lipoprotein cholesterol and triglycerides. Journal of Food Science (2000), 65(5):897-900. Abstract Only.
Hsiao G. et al., Inhibitory effects of lycopene on in vitro platelet activation and in vivo prevention of thrombus formation. Journal of Laboratory and Clinical Medicine (2005), 146(4):216-226.
Hua, J. Diagnosis and Treatment of Deep Venuous Thrombosis Formation in the Lower Limbs (with Analysis of 73 Cases). Zhejiang Medical Journal (1991). 13(6): 3-5.
Hwang et al., Effects of tomato paste extracts on cell proliferation, cell-cycle arrest and apoptosis in LNCaP human prostate cancer cells. BioFactors. 2005, 23:75-84.
Jerjes-Sanchez, C. Venous and arterial thrombosis: a continuous spectrum of the same disease? European Heart Journal. (2005) 26(1):3-4.
Kagome. An Agent used in foodstuffs and beverages for improving fatigue, comprises liquid squeezed from a tomato or component obtained by centrifuging squeezed tomato liquid. Database WPI—Publication No. JP 2006-193435 (Jul. 27, 2006). 1 page. Abstract Only.
Kloek et al. Effect of a Paste from Flavonoid-enriched Tomatoes on Blood Pressure in Spontaneously Hypertensive Rats. FASEB Journal (2004). 18(4-5). Abstract Only.
Lidder et al. Vascular effects of dietary intrate (as found in green leafy vegetables and beetroot) via the nitrate-nitrite-nitric oxide pathway. British Journal of Clinical Pharmacology (2012). 75(3):677-696.
Longo et al. Extract from Harrison's Principals of Internal Medicine. McGraw Hill Companies, Inc. 18th Edition (2012). 9 pages.
Lopez et al., Deep venous thrombosis. American Society of Hematology (2004), 439-456.
Lucking et al., Diesel Exhaust Inhalation Increases Thrombus Formation in Man, 2008, European Heart Journal, vol. 29(24), pp. 3043-3051.
Martini et al. Extract from Fundamentals of Anatomy and Physiology. Blood (2009) 8th Edition. Ch. 11. pp. 262-263.
Maruyama et al. Therapeutic strategy targeting coagulation factor Xa in thromboemobolism—Antithrombotic therapy by targeting Xa. Journal of Clinical and Experimental Medicine (2004). 208:393-395.
Miean et al., Flavonoid (myricetin, quercetin, kaempferol, luteolin, and apigenin) content of edible tropical plants. Medicinal & Aromatic Plants Abstracts. 2002, 24(1).
Moco et al. A Liquid Chromatography-Mass Spectrometry-Based Metabolome Database for Tomato. Plant Physiology (2006). 141:1205-1218.
Murphy et al. Whole Beetroot Consumption Actutely Improves Running Performance. J Acad Nutr Diet (2012). 112:548-552.
Naczk et al., Pheolics in cereals, fruits and vegetables: Occurrence, extraction and analysis. Journal of Pharmaceutical and Biomedical Analysis. 2006, 41(5):1523-1542. Abstract.
Nieman et al. Effects of Quercetin and EGCG on Mitochondrial Biogenesis and Immunity. Med Sci Sports Exerc (2009). 41(7):1467-1475.
O'Kennedy et al., Effects of antiplatelet components of tomato extract on platelet function in vitro and ex vivo: a time-course cannulation study in healthy humans. American Journal of Clinical Nutrition (2006), 84(3):570-579.

(56) References Cited

OTHER PUBLICATIONS

O'Kennedy et al., Effects of tomato extract on platelet function: a double-blinded crossover study in healthy humans American Journal of Clinical Nutrition (2006), 84(3): 561-569.

Oliff, H. Scientific and Clinical Monograph for Pycnogenol. Retrieved from internet: http://abc.herbalgram.org/site/DocServer/Pycnog_FullMono120809_LOW.pdf?docID=1741 on Jan. 1, 2010.

Paran et al. The Effects of Natural Antioxidants from Tomato Extract in Treated but Controlled Hypertensive Patients. Cardiovasc Drugs Ther (2009). 23:145-151.

Roth, GJ. Platelets and blood vessels: the adhesion event. Immunology Today (1992). 13(3):100-105.

Siddesha et al., Inhibition of Angiotensin Converting Enzyme (ACE) by Medicinal Plants Exhibiting Antihypertensive Activity, Recent Progress in Medicinal Plants, 2010, vol. 29, pp. 269-308, Abstract.

Slimestad et al., The Flavonoids of Tomatoes, 2008, Journal of Agricultural and Food Chemistry, vol. 56(7):2436-2441.

Stevenson et al., Comparison of the relative recovery of polyphenolics in two fruit extracts from a model of degradation during digestion and metabolism. Molecular Nutrition & Food Research. 2007, 51(8):939-945.

Talbott et al. Ironman Triathlon Recovery Enhanced by Dietary Supplementation. FASEB Journal (2007). 21(5). 1 page. Abstract Only.

Van Het Hof et al., Carotenoid bioavailability in humans from tomatoes processed in different ways determined from the carotenoid response in the triglyceride-rich lipoprotein fraction of plasma after a single consumption and in plasma after four days of consumption. Journal of Nutrition (2000), 130:1189-1196.

Weber M. et al. Enhance platelet aggregation with TRAP-6 and collagen in platelet aggregometry in patients with venous thromboembolism Thrombosis Research. (2002) 107(6):325-328.

Yamamoto et al., Tomatoes have natural anti-thrombotic effects. British Journal of Nutrition (2003), 90(6):1031-1038.

Yokoyama et al. New anti-platelet drug and anticoagulation drug—Differences from asprin, warfarin and heparin. Journal of Clinical and Experimental Medicine (2006). Supp vol. (Apoplexy): 17-22.

Zheng et al., Oxygen radicals absorbing capacity of phenolics in blueberries, cranberries, chokeberries, and lingonberries. Journal of Agricultural and Food Chemistry. 2003, 51(2).

Zhu T. et al. Three-Dimensional Reconstruction of Thrombus Formation during Photochemically Induced Arterial and Venous Thrombosis. Annals of Biomedical Engineering Society. (2003) 31(5):515-525.

Zhuang, Q. Blood Coagulation and Fibrinolysis. Chinese Journal of Medicine (1981). 2(11):10-13.

WATER SOLUBLE TOMATO EXTRACT PROTECTS AGAINST ADVERSE EFFECTS OF AIR POLLUTION

CROSS-REFERENCE TO RELATED APPLICATIONS

This application is a National Phase of International Application No. PCT/EP2017/077993 filed Nov. 2, 2017, currently pending, which designated the U.S. and that International Application was published under PCT Article 21(2) in English, the entirety of which is hereby incorporated by reference. This application also includes a claim of priority under 35 U.S.C. § 119(a) and § 365(b) to European patent application No. EP 16196794.8 filed Nov. 2, 2016, the entirety of which is hereby incorporated by reference.

BRIEF DESCRIPTION OF THE INVENTION

This invention relates to the use of a water-soluble tomato extract ("WSTE") to protect against adverse effects of air pollution on the body's cardiovascular system.

BACKGROUND OF THE INVENTION

Air pollution comes in many forms. A common type of pollution is referred to as "particulate air pollution", which contains pollution in the form of soot, gases and other matter which are in the form of tiny particles, termed "respirable particulate matter". Respirable particulate matter is categorized by size, such as below 10 or 2.5 microns aerodynamic diameter ($PM_{10}$ or $PM_{2.5}$, respectively), or as nanoparticles (less than 100 nm diameter, or $PM_{0.1}$). These particles often come from vehicle emissions, particularly diesel fuel, or from diesel-powered machinery.

It has been shown that particulate matter is able to enter the blood stream and induce cytotoxic and inflammatory responses, and there is a recognized link between exposure to diesel emissions and cardiovascular disease. However, the actual mechanism of how this is accomplished is still not fully understood. See Solomon et al 2013 *J. Thromb Haemost* 11: 325-34; Tabor et al 2016 *Particle and Fibre Toxicology* 13:6 DOI 10.1186/s12989-016-0116-x; Lucking et al 2008 *European Heart J* 29: 3043-3051; and Hunter et al 2014 *Particle and Fibre Technology* 11:62 DOI 10.1186/s12989-014-0062-4.

Air pollution is a mixture of particulate matter (PM) and gaseous components. Numerous studies show that exposure to PM air pollution has adverse effect on cardiovascular health (Miller et al. 2012, Pope et al. 2015). Platelet activity/reactivity is linked to an increased risk of cardiovascular diseases especially thrombosis and will also contribute to the development of atherosclerosis. Platelet activity/reactivity can be increased by a number of factors notably air pollution. Thus, PM has been shown to promote arterial thrombosis and atherosclerosis through increased platelet activation.

Not all platelet anti-aggregation agents work via the same pathway, nor are anti-aggregation agents responsive to all aggregation stimuli. For example, clopidrogel (an anti-platelet pharmaceutical used in the secondary prevention of cardiovascular complications of atherosclerosis) can inhibit adenosine 5'-diphosphate (ADP)-induced platelet aggregation but not platelet aggregation induced by collagen or thrombin. (see Weber et al 1999 *British J Pharmacology* 126: 415-420). PM may stimulate platelet aggregation via a physical mechanism in addition to a physiological mechanism (such as the mechanism seen in oxygen radical-induced aggregation).

Water soluble tomato extracts which are lycopene-free have been described; see, e.g. WO2010/049707; WO10/049709, and WO99/55350 (all by Provexis Natural Products, Ltd). They are commercially available from DSM Nutritional Products, Switzerland under the registered trademark FRUITFLOW and FRUITFLOW 2. They have been described as having anti-platelet aggregation abilities, which are presumed to be due to the presence of nucleosides and other active agents in the extracts, such as adenosine, caffeic acid derivatives including chlorogenic acid, and flavonoids such as rutin and quercetin-3,4-glycoside.

It would be desirable to have a safe, effective nutraceutical, food or food supplement, nutraceutical or medicament which could help ameliorate the effects of particulate air pollution.

DETAILED DESCRIPTION OF THE INVENTION

It has been found, in accordance with this invention, that a water soluble tomato extract can protect the cardiovascular system against the adverse effects brought on by exposure to particulate air pollution. Thus, the invention concerns the use of a water soluble tomato extract (WSTE) for the maintenance of a healthy cardiovascular system, and/or to prevent platelet aggregation brought on by interaction with air pollution particulate matter.

According to a first aspect of the invention there is provided a composition comprising a Water soluble tomato extract for use in maintaining cardiovascular health, lessening the risk of developing a cardiovascular health problem, or reducing the likelihood of worsening an existing cardiovascular health problem in a subject who is exposed, or is at risk of exposure, to particulate air pollution.

According to another aspect of this invention there is provided a method of maintaining cardiovascular health, lessening the risk of developing a cardiovascular health problem, or reducing the likelihood of worsening an existing cardiovascular health problem in a subject exposed, or is at risk of exposure, to particulate air pollution comprising administering a protective amount of a water soluble tomato extract prior to or concomitant with exposure to air pollution particulate matter.

Another aspect of this invention provides the use of WSTE in the manufacture of a medicament, nutraceutical, food supplement or food for use in maintaining cardiovascular health, lessening the risk of developing a cardiovascular health problem, or reducing the likelihood of worsening an existing cardiovascular health problem in a subject who is exposed, or is at risk of exposure, to particulate air pollution.

Another aspect of this invention provides a dosage form comprising a medicament, nutraceutical, food supplement or food comprising an effective amount of WSTE for protecting against the adverse effects of particulate air pollution.

The inventors believe that WSTE is effective for maintaining cardiovascular health because, as discussed below, WSTE decreases or minimizes the risk of platelet aggregation in a subject exposed to particulate air pollution. Thus, according to another aspect of the invention, there is provided a method of decreasing, or minimizing the risk of, platelet aggregation in a subject exposed to particulate air pollution comprising administering to the subject an effective amount of WSTE prior to or during exposure to particulate air pollution.

DEFINITIONS

As used in the specification and claims, the following definitions apply:

Water Soluble Tomato Extract ("WSTE"): The WTSE used in this invention has the following properties:

It is water soluble at room temperature, i.e. at 25° C. In preferred embodiments, the extracts also are soluble at lower temperatures as well (such as 15° C., 10° C. or even as low as 4° C., although more stirring over a longer period of time may be required). The WSTE contains substantially no, or only negligible quantities of lycopene (less than 0.5% by dry weight, preferably less than 0.1% by dry weight).

It is substantially free from water-insoluble particulate material (i.e. less than 0.1% by dry weight, preferably less than 0.01% by dry weight of particulate material).

It may be in liquid or dry forms. In some forms, such as in the dry extract FRUITFLOW 2, the sugars have been removed, and the extract has been concentrated.

Particulate Air Pollution: This is air pollution which contains particles which are classified as nanoparticles, or have a particle size of $PM_{2.5}$ or less. These size particles can be the result of "natural sources" such as volcanic emission, dust storms, forest fires, smoke from grassland fires and the like, or as a result of human activity such as automotive emissions, manufacturing emissions or other activities, including smoking.

Cardiovascular health: This term is defined as conditions associated with unwanted platelet aggregation, such as: arthrosclerosis, myocardial infarction, stroke, thrombosis, peripheral artery disease, or decreased cerebral blood flow, and also includes diabetes (Type I or Type 2) and its associated cardiovascular problems.

Healthy Person—for purposes of this invention, a healthy person has not been diagnosed with, nor is aware of any cardiovascular health problems which are related to unwanted platelet aggregation, arthrosclerosis, myocardial infarction, stroke, thrombosis, peripheral artery disease, decreased cerebral blood flow, or diabetes (either Type 1 or Type 2).

Preferred Compositions

A preferred WSTE comprises a tomato extract which is substantially lycopene-free, substantially heat stable and comprises water soluble compounds that have activity for preventing platelet aggregation and which have a molecular weight of less than 1000 daltons.

Preferably the WSTE comprises a, some or each of the water soluble compounds with activity for preventing platelet aggregation selected from the group comprising:

(a) glycosylated phenolic acids or phenolic esters, or derivatives thereof
(b) glycosylated flavonoids; and
(c) nucleosides.

Figure 2:
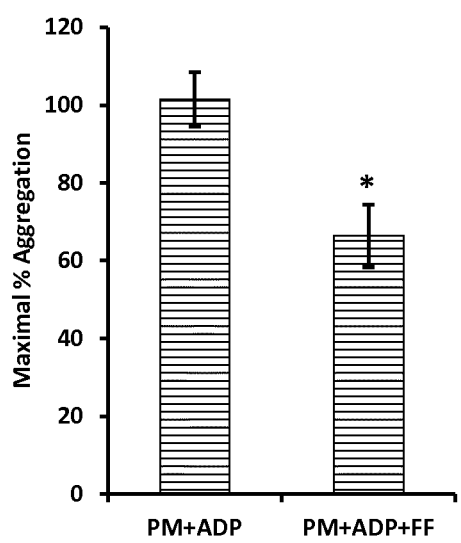
FIG. 2 shows the effect of FRUITFLOW on the amount of aggregation (maximal % aggregation induced by particulate matter and ADP (adenosine diphosphate)

It is preferred that the WSTE used according to the invention is a tomato extract described in WO2010/049707. Preferably the WSTE is made according to the methods described in WO2010/049707. For instance, in some embodiments the WSTE may be made according to the methods described in FIG. 2 or 4 of WO2010/049707.

In one embodiment the WSTE is a liquid in the form of a syrup.

A preferred extract has a browning index of <0.8 AU, a pH of 4.0-4.3 and a density of 1.15-1.20 and may be prepared by the steps of:

(a) Preparing a start mix of homogenised tomato;
(b) Separating a water soluble fraction from fruit solids;
(c) filtration of the water soluble fraction to make the extract substantially lycopene-free; and
(d) concentration of water soluble compounds with activity for preventing platelet aggregation in the filtration permeate using an evaporator.

In another embodiment sugars may be removed from the extract. It is preferred that such extracts contain <1% sugar, and contain >95% of the water soluble compounds with activity for preventing platelet aggregation that are contained in a start mix of homgenised tomatoes from which the WSTE is derived. Such extracts may be in the form of concentrated aqueous solutions or preferably in powder form. In a most preferred embodiment such an extract may be made by the steps of:

(a) Preparing a start mix of homogenised tomato fruit, wherein the pH of the start mix does not exceed pH 5.5, the holding temperature of the start mix does not exceed 35° C. and the start mix is diluted with water such that it comprises less than 33% solids;
(b) Separating a water soluble fraction from fruit solids by a procedure that does not raise the temperature of the fraction above 60° C.;
(c) filtration of the water soluble fraction;
(d) removal of free sugars from the filtered water soluble fraction; and
(e) concentration of water soluble compounds with activity for preventing platelet aggregation by a procedure that does not raise the temperature of the fraction above 60° C.;

Following step (e) the extract may be a concentrated aqueous solution containing <1% sugar, and containing >95% of water soluble compounds with activity for preventing platelet aggregation contained in the start mix. Such aqueous solutions may be dehydrated further to form a powder.

In some embodiments the WSTE may be provided in a composition that contains other molecules that are beneficial to human health. For instance, the composition may also contain nitrate or a precursor of nitric oxide. The nitrate is preferably from a source of dietary nitrate (for instance, and purely by way of example, a water-soluble extract from swiss chard, rocket, spinach, rhubarb, strawberry or lettuce). The composition may also comprise folic acid or a metabolite thereof (e.g. 5-methoxytetrahydrofolate or tetrahydrofolate). Preferred compositions for use according to the present invention which comprise folic acid or a metabolite thereof and/or nitrate are described in WO2014/102546.

Subjects that benefit from WSTE treatment are preferably human subjects. The inventors have found that healthy persons and those with a pre-existing cardiovascular condition can benefit from taking WSTE if they are at risk of being exposed to particulate air pollution.

Use in Healthy Persons

In some embodiments the person is a healthy person. In preferred embodiments where the person ingests the WSTE of this invention prior to exposure to air pollution, the ingestion occurs at least 30 minutes to 1 hour prior to the exposure. In particularly preferred embodiments, the ingestion occurs at least 2 or at least 3 hours prior to exposure in order to ensure the food or food supplement containing the WSTE has been digested and that the WSTE active ingredients have entered the circulatory system at their optimum levels. In areas where air pollution occurs in sustained episodes (i.e. air pollution lasts more than one day), the WSTE should be taken prior to the first episode and at least daily during the air pollution episode. In other embodiments, the WSTE is taken at least daily during the portion of the year where air pollution episodes are likely to occur.

Another embodiment of this invention is a method of maintaining healthy blood flow, or minimizing the risk of platelet aggregation in a person exposed to particulate air pollution comprising administering to the person at risk of exposure an effective amount of WSTE prior to or during exposure to particulate air pollution.

In another aspect of this invention the person at risk generally enjoys good cardiovascular health, i.e. does not have known problems associated with cardiovascular health.

Another embodiment of this invention is the use of WSTE to non-therapeutically maintain healthy blood flow in a healthy person at risk of exposure to particulate matter type air pollution. Examples of non-therapeutic results include: decreasing the risk of appearing older due to skin care issues, particularly wrinkles or hardening of the skin, and/or maintaining general well-being and balance of energies due to good blood circulation.

Other uses of the WSTE of this invention include:
Maintaining healthy platelet function in the presence of air pollution;
Maintaining a healthy blood circulation and blood flow in the presence of air pollution;
Reducing the risk of an adverse cardiovascular condition, such as atherosclerosis, or thrombosis in the presence of particulate matter air pollution;
Reducing the severity of cardiovascular diseases when exposed to particulate matter; and
Reducing the risk of cardiovascular and respiratory illness in an air polluted environment.

Use in Persons Who Already have Cardiovascular Disease

It has also been surprisingly found that WSTE shows a synergistic anti-platelet aggregation effect in the presence of both adenosine diphosphate (ADP) and PM. ADP, a natural platelet agonist stored in platelets, is released upon platelet activation; and it induces a strong initiation of platelet aggregation. PM also strongly induces platelet aggregation generally, and also further promotes the platelet aggregation induced by ADP. The combination of ADP plus PM is inducing a stronger platelet activation response than the sum of the individual platelet activation responses induced by ADP or PM alone. As shown in more detail in the Examples, we have found that WSTE inhibits both the platelet activity induced by PM present in air pollution, and surprisingly it also inhibits the ADP induced platelet aggregation when promoted by the presence of PM.

Thus the WSTE of this invention, if desired, can also be used in a population of people who have a history of cardiovascular health problems or diabetes, and therefore have ADP present in their circulating blood, and are also at risk of exposure to particulate air pollution. Thus, another embodiment of this invention is a method of maintaining cardiovascular health in persons who have a history of cardiovascular health problems and who are exposed to particulate air pollution or who are at risk of exposure to particulate air pollution comprising administering an effective amount of a WSTE extract to the person prior to exposure or during exposure to the particulate air pollution.

Another aspect of this invention is the use of WSTE to protect the user against the harmful cardiovascular effects of air pollution, preferably particulate matter air pollution. A person who is exposed to such air pollution or who is at risk of exposure to such air pollution can ingest WSTE and thereby protect him/herself against cardiovascular problems associated with air pollution.

Another aspect of this invention is a method of decreasing the risk of cardiovascular health problems associated with particulate air pollution induced platelet aggregation comprising administering WSTE to a person at risk of exposure to particulate air pollution.

Another aspect of this invention is the use of water soluble tomato extract for the use in manufacturing a pharmaceutical or nutraceutical capable of maintaining cardiovascular health, lessening the risk of developing a cardiovascular health problem, or reducing the likelihood of worsening an existing cardiovascular health problem in a person who is exposed or is at risk of exposure to particulate air pollution.

Dosages and Formulations

Doses:

Tomato Extract: Preferably, FRUITFLOW® 2 (a powder form) is used, although FRUITFLOW 1 (a liquid form) may be preferable if the formulation is to be liquid. The amount of WSTE should be from 25-300 mg/day preferably from 75-200 mg/day, and more preferably 125-175 mg/day. In some embodiments, 100 or 150 mg/day may be consumed by a subject. The aforementioned amounts may be taken as a single once-a-day dose, or partial dosages may be taken more than once a day (i.e. 2 or 3 times per day) so that the full dose is consumed. Preferred dosage forms according to the invention comprise 25-300 mg of WSTE, preferably 75-200 mg of WSTE and more preferably 125-175 mg of WSTE.

Timing of the dosage: It is preferable to consume WTSE prior to exposure to the air pollution episode, preferably at least 2-3 hours prior, so that the WTSE is properly metabolized and is available in the circulatory system prior to the exposure. In other embodiments, the ingestion occurs at least 30 minutes to 1 hour prior to the exposure. In areas where air pollution occurs in sustained episodes (i.e. air pollution lasts more than one day), the WSTE should be taken prior to the first episode and at least daily during the air pollution episode. In other embodiments, the WSTE is taken at least daily during the portion of the year where air pollution episodes are likely to occur.

Forms

In one embodiment the compositions of the invention may be in the form of a nutraceutical. The term "nutraceutical" as used herein denotes usefulness in both nutritional and pharmaceutical fields of application. Thus, nutraceutical compositions comprising WSTE can be used as supplements to food and beverages and as pharmaceutical formulations for enteral or parenteral application which may be solid formulations, such as capsules or tablets, or liquid formulations, such as solutions or suspensions.

The WSTE nutraceutical compositions according to the present invention may further contain protective hydrocolloids (such as gums, proteins, modified starches), binders, film-forming agents, encapsulating agents/materials, wall/shell materials, matrix compounds, coatings, emulsifiers, surface active agents, solubilising agents (oils, fats, waxes, lecithins etc.), adsorbents, carriers, fillers, co-compounds, dispersing agents, wetting agents, processing aids (solvents), flowing agents, taste-masking agents, weighting agents, gelling agents, gel-forming agents, antioxidants and antimicrobials.

The nutraceutical compositions according to the present invention may be in any galenic oral form containing a conventional carrier material that is suitable for administering to the body, e.g. in solid forms such as (additives/supplements for) food, food premix, fortified food, tablets, pills, granules, dragées, capsules and effervescent formulations, such as powders and tablets, or in liquid forms, such as solutions, emulsions or suspensions as e.g. beverages, pastes and oily suspensions. The pastes may be incorporated in hard- or soft-shell capsules, whereby the capsules feature e.g. a matrix of animal-derived gelatin, plant proteins or ligninsulfonate.

If the nutraceutical composition is a pharmaceutical formulation the composition further contains pharmaceutically acceptable excipients, diluents or adjuvants. Standard techniques may be used for their formulation, as e.g. disclosed in *Remington's Pharmaceutical Sciences,* 20th edition Williams & Wilkins, Pa., USA. For oral administration, tablets and capsules are preferably used which contain a suitable binding agent, e.g. gelatine or polyvinyl pyrrolidone, a suitable filler, e.g. lactose or starch, a suitable lubricant, e.g. magnesium stearate, and optionally further additives.

In some embodiments the compositions may be formulated for consumption as a food or drink. Examples of such foods or drinks are dairy products including, for example, margarines, spreads, butter, cheese, yoghurts or milk-drinks.

Other examples of foods that may be fortified with WSTE include bread, cereal bars, bakery items, such as cakes and cookies, and potato chips or crisps.

Beverages encompass non-alcoholic and alcoholic drinks as well as liquid preparations to be added to drinking water and liquid food. Non-alcoholic drinks are e.g., soft drinks, sports drinks, fruit juices, lemonades, teas and milk-based drinks. Liquid foods are e.g., soups and dairy products.

Nutraceutical compositions containing WSTE may be added to a soft drink, an energy bar, or a candy.

The non-limiting examples are presented to further illustrate the invention.

EXAMPLES

Example 1

Reagents:

Diesel Particulate Matter (Industrial Forklift, SRM2975) was from National Institute of Standards and Technology (Gaithersburg, Md., USA). Adenosine diphosphate (ADP), dimethyl sulfoxide (DMSO) and titanium(IV) oxide (TiO2) anatase were from Sigma (Saint-Louis, Mo.). Phosphate buffered saline (PBS) was from Invitrogen (Carlsbad, Calif.).

Preparation of Diesel Particulate Matter and TiO2:

Particles were suspended in DMSO and sonicated in a sonicating water bath for 5 min to minimize agglomeration. They were diluted at appropriate concentrations in PBS before use.

Platelet Aggregation Measurements:

Blood from healthy human volunteers was collected through Safety-Multifly® needle into Sodium Citrate S-Monovette® tubes (Sarstedt, Nümbrecht, Germany). Platelet-rich plasma (PRP) was obtained by centrifugation of citrated blood at 150 g for 15 min at 37° C. PRP were transferred into plastic tubes and left at 37° C. Remaining blood was centrifuged at 2000 g for 15 min at 37° C. to obtain platelet-poor plasma (PPP). Platelet counts were determined using a Sysmex cell counter (Norderstedt, Germany) and the platelet number in PRP was adjusted to $3 \times 10^8$ platelets/mL with autologous PPP. PRP were incubated with Fruitflow® 2 (86 µg/mL) or PBS at 37° C. for 10 min prior to stimulation. The PRP suspensions were stimulated with ADP (2.5 µM), diesel particulate matter (50 µg/mL) or $TiO_2$ (50 µg/mL) in the presence or absence of Fruitflow® and the platelet aggregation was monitored on a platelet aggregometer (APACT 4004, Labitec, Ahrensburg, Germany) for 10 min at 37° C. under stirring conditions. PPP was used to determine the baseline (100% aggregation). As particles can impact the light transmission, PPP with diesel particulate matter (50 µg/mL) or $TiO_2$ (50 µg/mL) was used as baseline in the presence of respectively diesel particulate matter or $TiO_2$. The platelet aggregation was quantified as area under the aggregation curve (AUC) and as the maximal percent aggregation (max % aggr.).

Results

ADP is a natural platelet agonist stored in platelets and is released upon platelet activation; it induces a strong initiation of platelet aggregation. Diesel particulate matter (PM) also strongly induces platelet aggregation. In contrast, non-polluted TiO2 particles did not induce significant aggregation at equivalent concentrations. Moreover PM further promoted the platelet aggregation induced by ADP. The combination of ADP plus PM is inducing a stronger platelet activation response than the sum of the individual platelet activation responses induced by ADP or PM alone.

Figure 1:
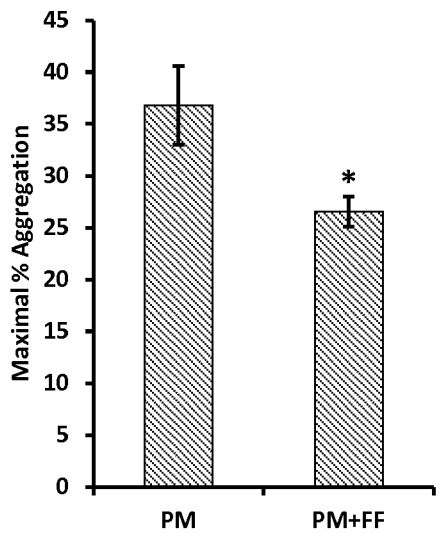
FIG. 1 shows the effect of FRUITFLOW on the amount of aggregation (maximal % aggregation) induced by particulate matter. Details are in the Examples.

Interestingly Fruitflow® was also able to inhibit the platelet aggregation induced by PM. Thus the area under the aggregation curve (AUC) was significantly decreased by 30% from 18606 to 13079. and the maximal percent aggregation (max % aggr.) was significantly decreased by 28% from 37% to 27% in the presence of Fruitflow® (Table 1 and FIG. 1). Finally, the platelet aggregation which is promoted by the combination of ADP and PM is strongly inhibited by Fruitflow®. The area under the aggregation curve (AUC) was significantly decreased by 36% from 55622 to 35511. The maximal percent aggregation (max % aggr.) was significantly decreased by 35% from 101% to 66% in the presence of Fruitflow® (Table 1 and FIG. 2)

TABLE 1

Effect of Fruitflow ® on platelet aggregation induced by air pollution particulate matter

|  | ADP | ADP + FF | PM | PM + FF | PM + ADP | PM + ADP + FF |
|---|---|---|---|---|---|---|
| AUC | 27953 ± 4856 | 6656 ± 1246* | 18606 ± 2207 | 13079 ± 683* | 55622 ± 3288 | 35511 ± 4297* |
| Max % aggr. | 54 ± 7 | 18 ± 5* | 37 ± 4 | 27 ± 1* | 101 ± 7 | 66 ± 8* |

All values are mean ± SD.
ADP, Adenosine diphosphate.
PM, particulate matter.
FF, Fruitflow ®.
AUC, area under the aggregation curve.
Max % aggr., maximal percent aggregation.
*$p < 0.05$ significantly different from the respective treatment not receiving FF (e.g. ADP vs. ADP + FF, PM vs PM + FF, PM + ADP vs PM + ADP + FF).

CONCLUSION

Fruitflow® inhibits the platelet activity induced by PM present in air pollution. Moreover, Fruitflow® also inhibits the ADP induced platelet aggregation when promoted by the presence of PM.

Thus, Fruitflow® reduces the platelet activation induced by PM which promote arterial thrombosis, atherosclerosis, and other cardiovascular diseases. Fruitflow® may be particularly useful in case of already elevated platelet reactivity due to stress. Furthermore, the WTSE can be used in persons with a preexisting disease such as diabetes or cardiovascular disease as the platelet reactivity which is increased by natural platelet agonist released under stress conditions and disease such as ADP are further promoted by air pollutants such as PM and can be inhibited by Fruitflow® such reducing the risk of cardiovascular events induced by PM. In conclusion, Fruitflow® is able to reduce the deleterious effects of PM on the cardiovascular system.

The invention claimed is:

1. A method of treating a human suffering from atherosclerosis, myocardial infarction, stroke, thrombosis or peripheral artery disease who is also exposed to particulate air pollution, consisting essentially of:
    administering a composition consisting essentially of a water soluble tomato extract to the human in need thereof,
    wherein at least one agent selected from the group consisting of rutin and quercetin-3,4-glycoside is in the water soluble tomato extract,
    wherein the lycopene content of the water soluble tomato extract is less than 0.5% by dry weight of the water soluble tomato extract, and the water insoluble particulate material is less than 0.1% by dry weight of the water soluble tomato extract, and
    wherein the water soluble tomato extract is made by a process consisting essentially of:
    a) preparing a start mix of homogenized tomato, wherein the pH of the start mix does not exceed pH 5.5, the holding temperature of the start mix does not exceed 35° C. and the start mix is diluted with water such that less than 33% tomato solids are in the start mix,
    b) separating a water soluble fraction from the solids of the tomato by a procedure that does not raise the temperature of the water soluble tomato fraction above 60° C. to yield a water soluble tomato fraction,
    c) filtration of the water soluble tomato fraction to remove particles larger than 1000 Daltons to yield a filtered water soluble tomato fraction,
    (d) concentration of water soluble compounds with activity for preventing platelet aggregation in the filtration permeate using an evaporator,
    e) removal of free sugars from the filtered water soluble tomato fraction,
    wherein the atherosclerosis, myocardial infarction, stroke, thrombosis or peripheral artery disease is effectively treated in the human in need thereof.

2. The method according to claim 1, wherein the water soluble tomato extract is in the form of a pharmaceutical, nutraceutical, food supplement or food.

3. The method according to claim 1, wherein the particulate air pollution is formed as a result of: volcanic emissions, dust storms, forest fires, smoke from grassland fires, automotive emissions, manufacturing emissions or smoking.

4. The method according to claim 1, wherein the water soluble tomato extract is a concentrated aqueous solution.

5. The method according to claim 1, wherein the water soluble tomato extract is in powder form.

6. The method according to claim 1, wherein a dosage form of the composition consists essentially of 25-300 mg of the water soluble tomato extract.

* * * * *